US008167900B2

(12) United States Patent
Teichert et al.

(10) Patent No.: US 8,167,900 B2
(45) Date of Patent: May 1, 2012

(54) ACUPUNCTURE DEVICE

(76) Inventors: Klaus Teichert, Pullach (DE); Elmar Grandy, Oberschleissheim (DE)

( * ) Notice: Subject to any disclaimer, the term of this patent is extended or adjusted under 35 U.S.C. 154(b) by 398 days.

(21) Appl. No.: 12/147,866

(22) Filed: Jun. 27, 2008

(65) Prior Publication Data

US 2009/0043329 A1 Feb. 12, 2009

(30) Foreign Application Priority Data

Jun. 29, 2007 (DE) .................... 20 2007 009 130 U

(51) Int. Cl.
*A61B 17/34* (2006.01)

(52) U.S. Cl. ....................................... 606/189; 606/167

(58) Field of Classification Search .................. 606/189, 606/185, 108, 194, 167

See application file for complete search history.

(56) References Cited

U.S. PATENT DOCUMENTS

| | | | | |
|---|---|---|---|---|
| 3,856,019 | A * | 12/1974 | Waller | 606/189 |
| 4,950,279 | A * | 8/1990 | Chang | 606/189 |
| 6,447,522 | B2 * | 9/2002 | Gambale et al. | 606/108 |

FOREIGN PATENT DOCUMENTS

| | | | |
|---|---|---|---|
| DE | 10 2006 007 803 | A1 | 8/2007 |

* cited by examiner

*Primary Examiner* — Ryan Severson
*Assistant Examiner* — Tin Nguyen
(74) *Attorney, Agent, or Firm* — Sughrue Mion, PLLC

(57) ABSTRACT

An acupuncture device includes an acupuncture needle which has an elongate grip part with a substantially cylindrical main portion and a needle part which is fixed to the distal end of the grip part such that its longitudinal axis is aligned with the grip part and a guide tube which is open at both ends and whose lumen has a substantially cylindrical main portion and a releasable clamping device, by means of which the acupuncture needle is held in the condition of readiness for use inside the guide tube so that the grip part projects outwardly out of the proximal end of the guide tube while the distal end of the guide tube extends beyond the tip of the needle part. The grip part further has a portion which is thickened in relation to its main portion and the lumen of the guide tube has a narrowed portion which adjoins the proximal end of its main portion and whose smallest inside diameter is smaller than the largest outside diameter of the thickened portion of the grip part and larger than the outside diameter of the cylindrical main portion of the grip part, wherein the clamping device is formed by the thickened portion of the grip part and the narrowed portion of the lumen of the guide tube.

2 Claims, 3 Drawing Sheets

ACUPUNCTURE DEVICE

Figure 1:
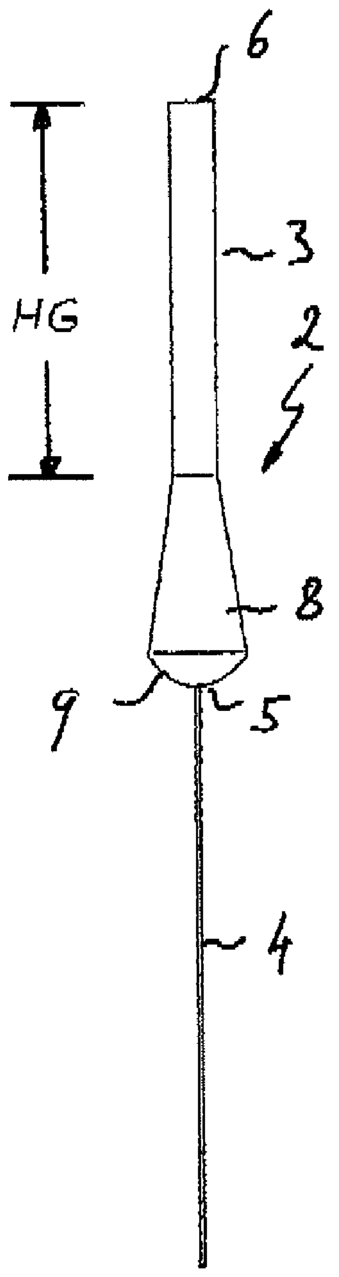

The invention concerns an acupuncture device of the kind set forth in the classifying portion of claim 1.

Such an acupuncture device can be found for example in prior German patent application No 10 2006 007 803.9.

The device described therein comprises substantially three main components. The acupuncture needle which comprises an elongate grip part in the form of a circular cylinder and a needle part which is fixed to the grip part in such a way that it projects out of the distal end thereof and its longitudinal axis is aligned with that of the grip part. That device also has a guide tube which is open at both ends and in the lumen of which, which is substantially in the shape of a circular hollow cylinder, the acupuncture needle is received in a condition of being ready for use, in such a way that the grip part projects with its proximal end out of the proximal end of the guide tube while the distal end of the guide tube extends beyond the tip of the needle part. To keep the acupuncture needle connected to the guide tube in that position, as a third component the arrangement has a clamping device, by means of which the needle and the guide tube are connected together fixedly but in an easily releasable fashion.

In that way it is possible for the guide tube firstly to be placed with its distal end on the location on the surface of the body of a patient, at which the acupuncture needle is to be caused to penetrate therein, in order then to release the clamping device so that the acupuncture needle can be displaced in the lumen of the guide tube towards the distal end thereof.

The clamping device can either be in the form of a separate component part or it can be movably integrally connected to the proximal end of the guide tube. In both cases it is necessary to exert forces extending transversely with respect to the longitudinal axis of the acupuncture device to release the clamping connection, which in the worst case can lead to displacement of the point of placement of the distal end of the guide tube. In addition the production of an additional component part or an element pivotably connected to the proximal end of the guide tube is comparatively complicated and expensive and increases the costs involved.

In comparison, the object of the invention is to provide an acupuncture device of the kind set forth in the opening part of this specification, in which only axially directed forces have to be applied to release the clamping connection between the guide tube and the acupuncture needle and which can be produced in a very simple and inexpensive fashion.

To attain that object, the invention provides the features set forth in combination in claim 1.

By virtue of the fact that, in accordance with the invention, the clamping device is formed by a thickened portion of the grip part of the acupuncture needle on the one hand and a narrowed portion of the lumen of the guide tube made from a preferably elastically deformable material on the other hand, which are designed as set forth in the characterising portion of claim 1, it is possible to release the clamping connection by a slight axial pressure on the end of the grip part, that projects from the proximal end of the guide tube, so that the acupuncture needle can move freely in the lumen of the guide tube towards the surface of the skin of the patient. There is no need for force to be applied in a radial direction.

A particular advantage of the device according to the invention is that both the thickening of the grip part of the acupuncture needle and also the reduction in the lumen of the guide tube can be absolutely radially symmetrical with respect to the longitudinal axis of the acupuncture needle or the guide tube so that it is possible to use very simple production tools, in particular casting moulds. There is no need for a third component. The manufacturing costs of an acupuncture device according to the invention are thus markedly reduced in comparison with the device described in the opening part of this specification and are only immaterially higher than those involved in the production of acupuncture needles, the grip part of which is of a circular-cylindrical configuration throughout and guide tubes whose lumen is of a hollow circular-cylindrical form throughout.

In a particularly preferred embodiment the thickened portion of the grip part is of a frustoconical shape and adjoins, preferably with a continuous transition, the distal end of the circular-cylindrical main portion of the grip part, in such a way that the two longitudinal axes are mutually aligned and the frustoconically thickened portion narrows towards the main portion of the grip part.

Accordingly, in this particularly preferred embodiment, the narrowed portion of the lumen is in the form of a truncated hollow cone which is arranged in the proximity of the proximal end of the guide tube and which at its enlarging distal end goes into the main portion of the lumen.

The apex angles of the frustoconical thickened portion of the grip part and the hollow-frustoconical portion of the lumen are approximately the same so that, for producing the clamping connection, it is sufficient for the acupuncture needle to be inserted with its proximal end leading into the distal end of the guide tube and displaced towards the proximal end of the guide tube until the frustoconical thickened portion of the grip part of the acupuncture needle enlarges the hollow-frustoconical narrowed portion of the lumen, which is readily possible by virtue of the elastically deformability of the material from which the guide tube is made. When the acupuncture needle is pushed sufficiently far into the guide tube in the manner just described above, the radially directed clamping forces exerted by the elastically expanded wall portion of the guide tube are readily sufficient to reliably fix the acupuncture needle in that position in the guide tube as long as no axially directed forces are exerted on the proximal end of the grip part of the acupuncture needle, while the guide tube is held fast at the same time.

It is therefore readily possible for the acupuncture unit which is formed in that way, in a sterile condition, to be packaged, transported and stored and in use thereof to be removed from the sterile packaging without the acupuncture needle and the guide tube separating from each other. It is only when the guide tube is placed with its distal end leading on the desired location on the surface of the body of a patient that separation is effected by an axial pressure on the proximal end of the grip part.

In a further preferred embodiment the thickened portion of the grip part is of a substantially spherical configuration and is preferably arranged at the distal end of the main portion of the grip part. With this embodiment the narrowed portion of the lumen can be formed by a projection which projects slightly inwardly from the cylindrical inside wall of the main portion of the lumen and which is preferably in the form of a ridge extending over the entire inside periphery of the lumen. Alternatively however it can also be formed by one or more projections involving a smaller angular extent.

With this variant, in manufacture of the acupuncture device according to the invention, for the purposes of making the clamping connection, the acupuncture needle is introduced with the needle tip leading into the proximal end of the guide tube and displaced towards the distal end until the spherical thickened portion comes to bear against the inwardly projecting projection.

In order to ensure that the acupuncture needle cannot move unintentionally out of the guide tube again in the opposite direction, there is preferably provided a second projection which projects inwardly from the cylindrical inside wall of the main portion of the lumen and which is arranged between the first projection and the proximal end of the guide tube at a spacing from the first projection, the size of which permits the spherically thickened portion to be received between the two projections without involving substantial deformation of the geometry of the guide tube. When the acupuncture needle is introduced into the guide tube, when the spherically thickened portion has reached the second projection which is closer to the proximal end of the guide tube, an axially directed force then has to be exerted in order to expand the elastically yielding wall of the guide tube until the spherically thickened portion has passed through the constriction formed by the second projection and has come to bear against the first inwardly projecting projection.

The second inwardly projecting projection can also be either in the form of a ridge extending around the entire inside periphery or it can be in the form of one or more individual projections of smaller angular extent, These and further advantageous configurations of the acupuncture device according to the invention are set forth in the appendant claims.

Figure 2:
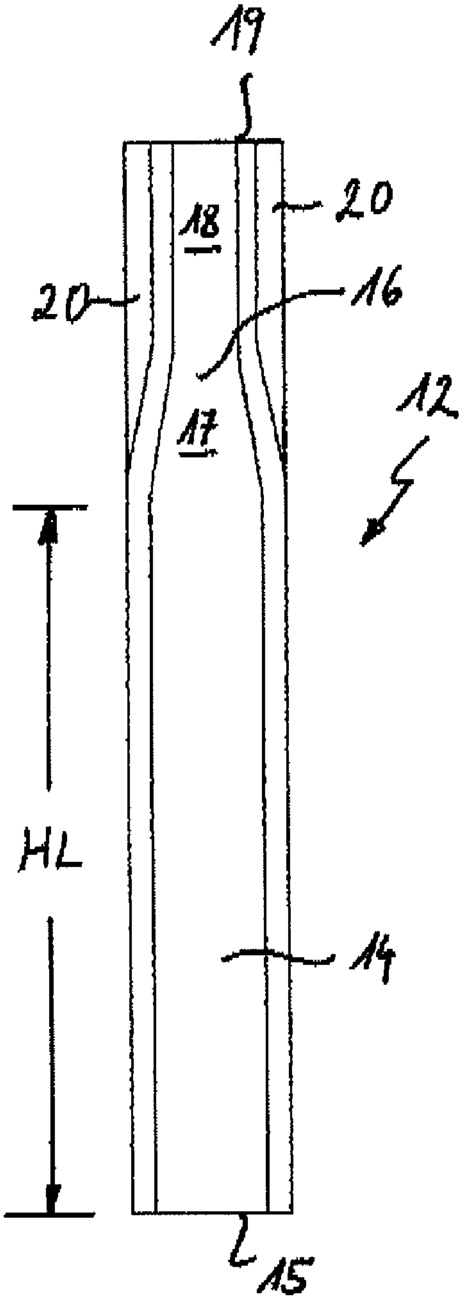
Figure 5:
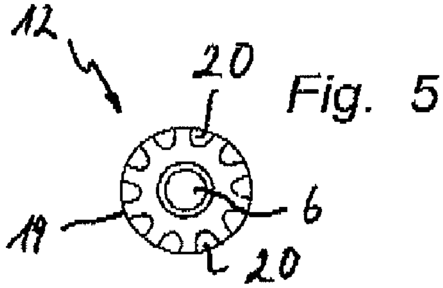
Figure 3:
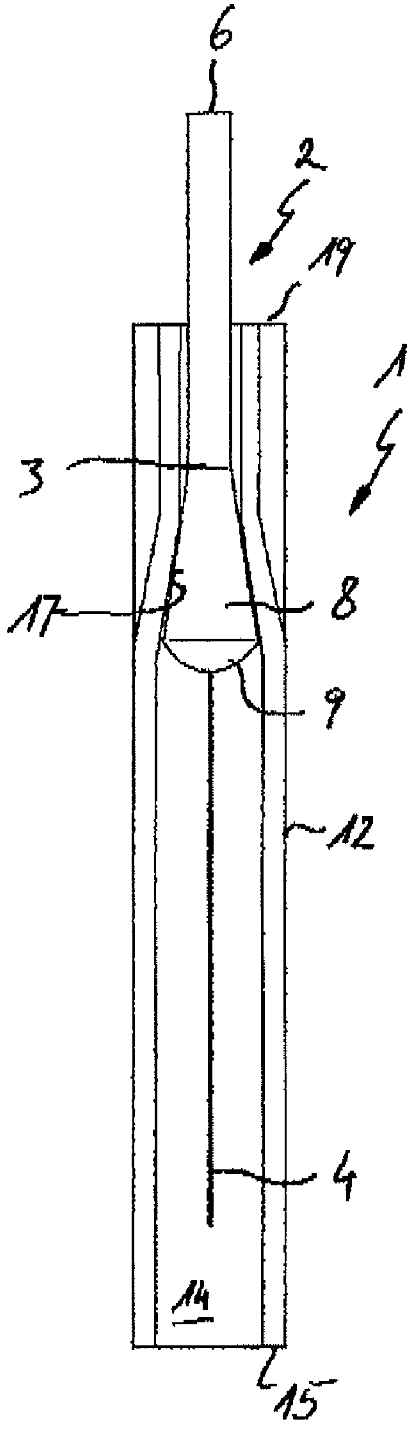
Figure 4:
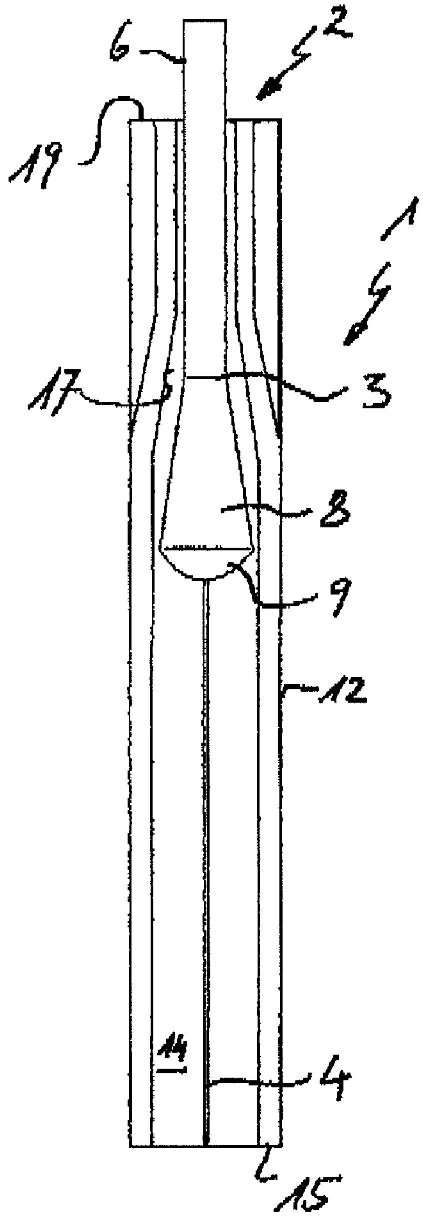
Figure 6:
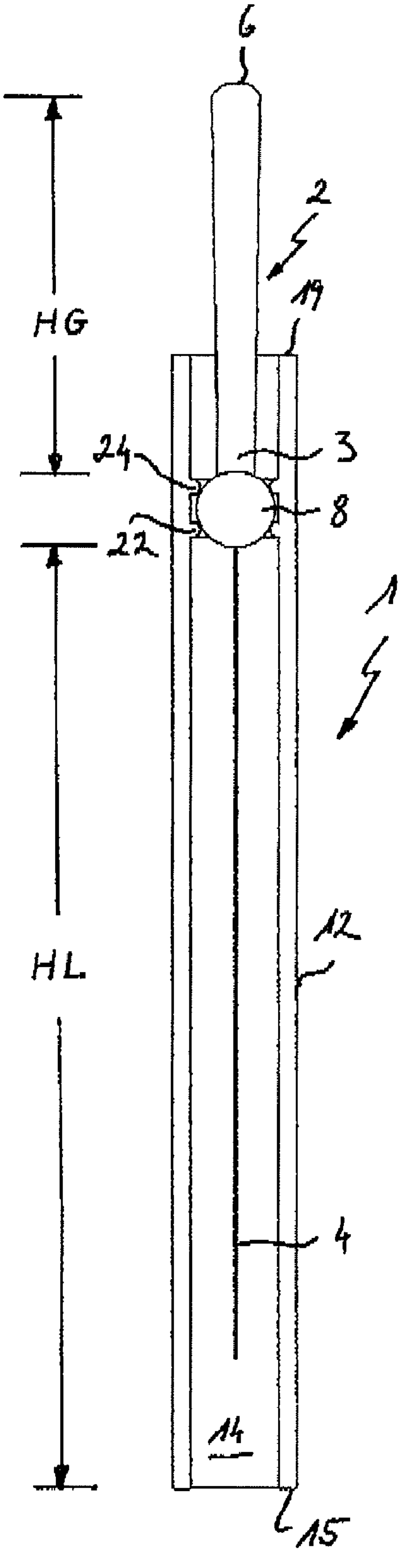
Figure 7:
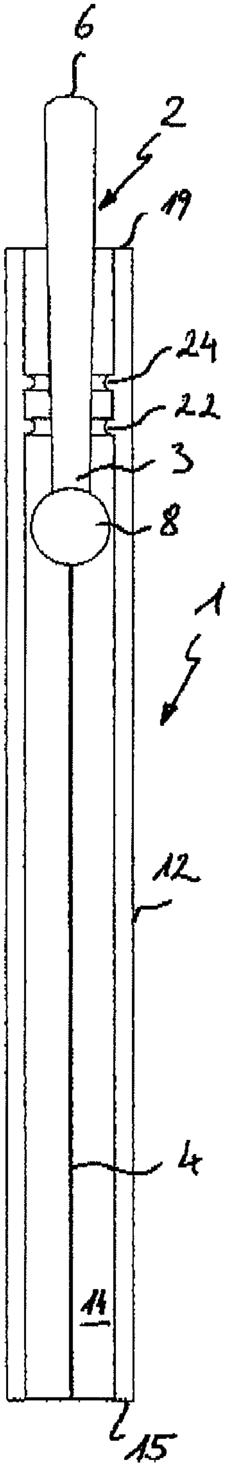

The invention is described hereinafter by means of embodiments by way of example with reference to the drawing in which:

FIG. 1 shows a first embodiment of an acupuncture needle according to the invention, FIG. 2 shows a view in longitudinal section through a guide tube belonging to the acupuncture needle of FIG. 1, FIG. 3 shows a view in longitudinal section through an acupuncture device according to the invention in the condition of being ready for use, which is formed by the acupuncture needle of FIG. 1 and the guide tube of FIG. 2, FIG. 4 shows the embodiment of the acupuncture device according to the invention of FIG. 3 immediately after release of the acupuncture needle, FIG. 5 shows a view from above of the embodiment illustrated in FIGS. 3 and 4, FIG. 6 shows a sectional view corresponding to FIG. 3 through a second embodiment of an acupuncture device according to the invention, and FIG. 7 shows a sectional view corresponding to FIG. 4 through the embodiment of FIG. 6.

In the Figures, identical or mutually corresponding parts are denoted by the same references. The references to 'distal' and 'proximal' relate to the orientation involved in use of the acupuncture device, the proximal end of which is closer to the therapist upon placement of the needle while its distal end faces away from him and is directed towards the patient.

As can be seen from FIGS. 1 to 5 a first embodiment of an acupuncture device 1 according to the invention includes an acupuncture needle 2 having an elongate grip part 3 and a needle part 4 which is fixed to the distal end 5 of the grip part 3 in such a way that its longitudinal axis is aligned with that of the grip part 3.

The grip part 3 has a substantially cylindrical main portion HG which is of a circular cross-section and which extends to the proximal end 6 of the grip part 3, and a thickened portion 8 which adjoins the distal end of the cylindrical main portion HG and which in this embodiment is in the form of a truncated cone and is arranged coaxially relative to the main portion HG in such a way that it enlarges away therefrom. Its smallest outside diameter is approximately equal to the outside diameter of the main portion HG while its largest outside diameter can be approximately two to three times as large. At its distal end the thickened portion 8 is rounded by a part-spherical portion 9, from the apex point of which the needle part 4 projects.

In addition the acupuncture device 1 includes a hollow guide tube 12 which is open at both ends and which on its outside is of a substantially circular-cylindrical configuration over its entire length and which is made from an elastically deformable material, preferably a suitable plastic material.

The lumen 14 of the guide tube 12, starting from the distal end 15 thereof, has a hollow circular-cylindrical main portion HL and an adjoining narrowed portion 16 which comprises a hollow frustoconical first sub-portion 17 and a hollow circular-cylindrical second sub-portion 18, which are arranged coaxially relative to each other in such a way that the main portion HL is firstly adjoined by the first sub-portion 17 and disposed adjoining same is the second sub-portion 18 which extends to the proximal end 19 of the guide tube 12. The first sub-portion 17 narrows from the main portion HL of the lumen 14 towards the second sub-portion 18, wherein the largest inside diameter of the first sub-portion 17 is approximately equal to the inside diameter of the main portion HL of the lumen 14 and its smallest inside diameter is approximately equal to that of the second sub-portion 18.

The narrowed portion 16 of the lumen 14 is formed by the wall thickness of the guide tube 12 continuously increasing from its value which is constant in the region of the main portion HL, in the region of the first sub-portion 17, in order then in the region of the second sub-portion 18 to again remain constant at a value which is approximately equal to double the wall thickness of the main portion HL.

As can be seen in particular from FIG. 5 in the region of that enlarged wall thickness a plurality of (in the illustrated example ten) grooves 20 extending in the axial direction are formed from the outside in the wall of the guide tube 12, the grooves 20 being arranged distributed at equal angular spacings around the outside periphery of the guide tube 12. In that respect the external shape of the guide tube 12 deviates from that of an exact circular cylinder. Those grooves 20 serve to improve the grippiness of the guide tube 12 in the region of its proximal end 19.

FIG. 3 shows the two parts of the first embodiment of an acupuncture device 1 according to the invention, namely the acupuncture needle 2 of FIG. 1 and the guide tube 12 of FIG. 2, in the assembled condition of readiness for use. As will be seen, the proximal end 6 of the main portion HG of the grip part 3 of the acupuncture needle 2 projects outwardly out of the proximal end 19 of the guide tube 12 while the distal end 15 of the guide tube 12 extends beyond the distal end of the needle part 4 and in so doing performs a protective function against unwantedly touching the needle part 4 or by mistake causing it to penetrate into a body.

The thickened frustoconical portion 8 of the grip part 3 is inserted in the axial direction towards the proximal end 19 of the guide tube 12 into the latter to such an extent that it elastically outwardly expands the hollow frustoconical first sub-portion 17 of the narrowed portion 16 of the lumen 14 so that the wall of the guide tube 12, in that region, exerts a clamping action on the grip part 3 of the acupuncture needle 2 whereby the latter is securely held fast in the guide tube 12 so that, even in the event of severe vibration as can occur upon transport and storage but also in preparation for use of the acupuncture device 1 according to the invention, it is not released from that holding action.

When however the guide tube 12 is placed with its distal end 15 on the location on the body of a patient into which the acupuncture needle 2 is intended to penetrate, a slight axial pressure or thrust on the proximal end 6 of the grip part 3 is sufficient to release the acupuncture needle 2 from its hold in the guide tube 12 so that it is displaced towards the distal end 15 of the guide tube to such an extent that the needle tip now also bears against the skin of the patient.

As the overall length of the acupuncture needle 2 in relation to the overall length of the guide tube 12 is such that the proximal end 6 of the grip part 3 projects out of the proximal end 19 of the guide tube 12 even in that situation, the needle can then be definitively placed and the guide tube 12 can be readily withdrawn over the proximal end of the acupuncture needle 2 because, between the location at which the maximum outside diameter of the thickened portion 8 of the grip part 3 is now disposed and the distal end 15 of the guide tube 12, the inside diameter of the lumen 14 is everywhere larger than the maximum outside diameter of the thickened portion 8 and in the other axial regions the inside diameter of the lumen 14 is everywhere larger than the outside diameter of the cylindrical main portion HG of the grip part 3.

A corresponding consideration also applies in entirely similar manner to the embodiment shown in FIGS. 6 and 7, in which the thickened portion 8 of the grip part 3 is of a spherical configuration and the narrowed portion 16 of the lumen 14 is formed by a peripheral ridge 22 which projects inwardly from the inside wall of the lumen 14 and which is disposed on the distal side of the thickened portion 8 in the condition shown in FIG. 6 of being ready for use.

So that the acupuncture needle 2 cannot drop out of the guide tube in the proximal direction in this embodiment, a second peripheral ridge 24 is arranged at such an axial spacing from the first peripheral ridge 22 towards the proximal end 19 of the guide tube that the thickened portion 8 can be received and held between those two peripheral ridges 22, 24.

A further difference in relation to the embodiment of FIGS. 1 to 5 is that in this case permanent elastic deformation of the wall of the guide tube 12 does not have to be effected in the condition of readiness for use. That expanding deformation then occurs only during assembly of the device 1 at the peripheral ridge 24 and in use at the peripheral ridge 22, in each case only during the short period of time during which the spherical thickened portion 8 is being pushed through the respective constriction by an axially directed force being applied to the projecting proximal end 6 of the grip part 3.

Instead of the described conical or spherical form the thickened portion 8 can also be of any other suitable shape. The local constriction of the lumen of the guide tube can also be produced in a different fashion than by the provision of a frustoconical narrowing or an inwardly projecting projection.

The material from which the grip part of the acupuncture needle is made can also enjoy a certain elastic deformability which however is preferably less than that of the material of the guide tube. Preferably all materials used are easy to sterilise and are resistant to the sterilisation methods usual in the medical-technical field, for example by irradiation (γ-or x-rays or the like) and/or gassing (for example with ethylene oxide) and/or heating.

The invention claimed is:

1. An acupuncture device which includes the following:

an acupuncture needle (2) which has an elongate grip part (3) with a substantially cylindrical main portion (HG) and a needle part (4) which is fixed to the distal end of the grip part (3) in such a way that its longitudinal axis is aligned with the grip part (3), a guide tube (12) which is open at both ends and whose lumen (14) has a substantially cylindrical main portion (HL), and a releasable clamping device, by means of which the acupuncture needle (2) is held in the condition of readiness for use in the lumen (14) of the guide tube (12) so that the grip part (3) of the acupuncture needle (2) projects outwardly out of the proximal end (19) of the guide tube (12) while the distal end (15) of the guide tube (12) extends beyond the tip of the needle part (4), said grip part (3) further having one single portion (8) which is thickened in relation to the main portion (HG) of the grip part (3), said thickened portion (8) being of a substantially spherical configuration and being arranged at the distal end of the main portion (HG) of the grip part (3), said lumen (14) of said guide tube (12) having a narrowed portion (16) which is formed by a first ridge (22) projecting inwardly with respect to the cylindrical inside wall of the main portion (HL) of said lumen (14) and being arranged at a distance from the proximal end of said main portion (HL), the smallest inside diameter of said narrowed portion (16) being smaller than the largest outside diameter of the thickened portion (8) of the grip part (3) and being larger than the outside diameter of the cylindrical main portion (HG) of the grip part (3), a second inwardly projecting ridge (24) being provided at the cylindrical inside wall of said main portion (HL) of said lumen (14) and being arranged towards the proximal end (19) of said guide tube (12) at an axial spacing from said first inwardly projecting ridge (22) which axial spacing is smaller than the axial length of said spherical thickened portion (8) of said grip part (3), whereby said thickened portion (8) can be received between and simultaneously contacted by said two ridges (22, 24), the clamping device being formed by the thickened portion (8) of the grip part (3) and the narrowed portion of the lumen (14) of the guide tube (12) which thickened portion is located between said first and second inwardly projecting ridges (22, 24), the guide tube (12) is made from a deformable material, and the difference between the largest outside diameter of the thickened portion (8) of the grip part (3) and the smallest inside diameter of the narrowed portion (16) of the lumen (14) is so small that the clamping action can be overcome by exerting a slight axial force on the projecting proximal end (6) of the grip part (3).

2. An acupuncture device according to claim 1 characterised in that the inwardly projecting ridges (22, 24) extend over the entire inside periphery of the lumen (14).

* * * * *